(12) United States Patent
Naughton et al.

(10) Patent No.: US 6,814,738 B2
(45) Date of Patent: Nov. 9, 2004

(54) MEDICAL IMPACTING DEVICE AND SYSTEM

(75) Inventors: Ronald J. Naughton, South Dartmouth, MA (US); Danielle Sheeran, Westwood, MA (US)

(73) Assignee: Depuy Acromed, Inc., Raynham, MA (US)

( * ) Notice: Subject to any disclaimer, the term of this patent is extended or adjusted under 35 U.S.C. 154(b) by 0 days.

(21) Appl. No.: 10/046,920

(22) Filed: Jan. 15, 2002

(65) Prior Publication Data

US 2002/0107523 A1 Aug. 8, 2002

Related U.S. Application Data (60) Provisional application No. 60/263,427, filed on Jan. 23, 2001.

(51) Int. Cl.⁷ .............................................. A61B 17/58
(52) U.S. Cl. ...................................................... 606/100
(58) Field of Search ............................ 606/100, 99, 53; 279/102; 173/90

(56) References Cited

U.S. PATENT DOCUMENTS

| | | | |
|---|---|---|---|
| 530,866 A | | 12/1894 | Vanhouten |
| 1,384,330 A | * | 7/1921 | Moshier ..................... 606/100 |
| 3,834,393 A | | 9/1974 | Goggins |
| 4,101,088 A | * | 7/1978 | Stauth ..................... 242/396.1 |
| 4,153,053 A | | 5/1979 | Figallo E |
| 4,423,721 A | | 1/1984 | Otte et al. |
| 4,877,020 A | | 10/1989 | Vich |
| 4,919,679 A | * | 4/1990 | Averill et al. ............... 606/100 |
| 4,971,479 A | | 11/1990 | Byers, Sr. et al. |
| 4,993,410 A | | 2/1991 | Kimsey |
| 5,078,718 A | | 1/1992 | Moll et al. |
| 5,282,804 A | | 2/1994 | Salyer |
| 5,476,467 A | | 12/1995 | Benoist |
| 5,534,006 A | | 7/1996 | Szabo et al. |
| 5,741,253 A | | 4/1998 | Michelson |
| 5,797,917 A | | 8/1998 | Boyd et al. |
| 5,800,546 A | | 9/1998 | Marik et al. |
| 5,913,860 A | | 6/1999 | Scholl |
| 5,918,501 A | * | 7/1999 | Sunaga et al. ................. 72/479 |
| 5,934,139 A | * | 8/1999 | Tucker ........................ 72/479 |
| 6,022,357 A | | 2/2000 | Reu et al. |
| 6,063,124 A | * | 5/2000 | Amstutz ................... 623/22.21 |
| 6,096,038 A | | 8/2000 | Michelson |
| 6,139,551 A | | 10/2000 | Michelson et al. |
| RE37,005 E | | 12/2000 | Michelson et al. |
| 6,156,040 A | | 12/2000 | Yonemura et al. |
| 6,474,198 B2 | * | 11/2002 | Lowther ......................... 81/27 |

FOREIGN PATENT DOCUMENTS

| | | |
|---|---|---|
| DE | 1246162 | 8/1967 |
| DE | 20012735 | 10/2000 |
| EP | 0780090 | 6/1997 |
| EP | 0780092 | 6/1997 |
| EP | 0780906 | 6/1997 |
| WO | WO 92/05742 | 4/1992 |

* cited by examiner

*Primary Examiner*—Michael J. Milano
*Assistant Examiner*—Jessica R Baxter
(74) *Attorney, Agent, or Firm*—Nutter, McClennen & Fish LLP (57) ABSTRACT

A force applying surgical system is provided for use to assist in the insertion and/or removal of a surgical tool or a device attached thereto from an orthopedic structure. This surgical system comprises a medical impacting device that mates with a surgical tool such that the impacting device can be manually reciprocated along an axis of the tool to forcefully impact the impacting device on a portion of the tool. The impacting device can generate a distally directed force for inserting the tool (and/or an attached device) into an orthopedic structure, or it can generate a proximally directed force to remove the tool (and/or attached device) from an orthopedic structure.

19 Claims, 5 Drawing Sheets

MEDICAL IMPACTING DEVICE AND SYSTEM

CROSS REFERENCE TO RELATED APPLICATIONS

This application claims priority from U.S. Provisional Patent Application Ser. No. 60/263,427, filed on Jan. 23, 2001, entitled "Medical Impacting Device and System," which is expressly incorporated by reference herein.

FIELD OF THE INVENTION

The present invention relates to medical tools that assist in orthopedic, and in particular spinal, surgical procedures. More particularly, the invention relates to tools that may be easily and safely inserted and removed from spaces between joints or prostheses, or between adjacent bone structures, and to tools that assist in the insertion or removal of other tools or devices from locations within joints or prostheses, or between adjacent bone structures.

BACKGROUND OF THE INVENTION

Advancing age, as well as injuries, can lead to changes in the various bones, discs, joints and ligaments of the body. In particular, these changes can manifest themselves in the form of damage or degeneration of an intervertebral disc, the result of which is mild to severe chronic back pain. Intervertebral discs serve as "shock" absorbers for the spinal column, absorbing pressure delivered to the spinal column. Additionally, they maintain the proper anatomical separation between two adjacent vertebra. This separation is necessary for allowing both the afferent and efferent nerves to exit and enter, respectively, the spinal column.

Treatment for a diseased or damaged disc can involve the removal of the affected disc and subsequent fusion of the opposing vertebra to one another. Spinal fusion consists of fusing the adjacent vertebrae through the disc space (the space previously occupied by the spinal disc interposed between the adjacent vertebral bodies). Typically, a fusion cage and/or bone graft is placed into the disc space to position the vertebrae apart so as to create more space for the nerves, to restore the angular relationship between the adjacent vertebrae to be fused, and to provide for material that can participate in and promote the fusion process.

Several different tools have been developed to facilitate the preparation of the adjacent vertebral bodies, as well as the subsequent placement and/or removal of an implant between adjacent bone structures. Typically, prior to insertion of an implant, bone preparation tools are used to prepare the bone surfaces of the adjacent vertebrae. Mallets are often used to apply an impacting force on a medical tool, such as a chisel, to remove bone from a vertebral body. Mallets are also commonly used to insert an implant, and to remove tools positioned between adjacent vertebrae. While mallets are effective, the impacting force must be axially applied to avoid misalignment of the prosthesis, or the inadvertent removal of bone. Moreover, the force applied must be sufficiently accurate to avoid damage to the vertebrae.

To overcome some of these problems, slap hammers have been developed and are widely used in orthopedic procedures to apply an impacting force on various tools used during surgery. However, most slap hammer designs still have several drawbacks. Current slap hammers are typically only used for removal of medical devices and tools, and tend to be very large and heavy, and are thus difficult to handle. Exceptional care must be exercised while using these instruments to prevent injury to the patient and/or the surgeon. In particular, the surgeon's hands can be pinched between the hammer portion of the instrument and the hammer stops. Care must also be exercised to prevent accidental disengagement of the slap hammer from the device.

Accordingly, there remains a need for an improved slap hammer device which can be safely and effectively used to apply both an insertion and removal force to a medical tool.

SUMMARY OF THE INVENTION

The present invention pertains to a force applying surgical system which includes a medical impacting device and a surgical tool. The medical impacting device can be selectively mated with a variety of surgical tools, and is effective to enable a surgeon to provide a force in a desired direction to either insert or remove the associated surgical tool (or a device attached to the tool) from an orthopedic structure. The medical impacting device is a slidable mass which can engage the surgical tool in a removable, replaceable manner. This medical impacting device can be selectively reciprocated along an axis of the surgical tool.

In one embodiment, a surgical system is provided including an elongate surgical tool having a handle portion and a distal portion extending therefrom, and a substantially cylindrical impacting device, e.g. a hollow slidable mass, removably and replaceably disposed around the handle portion of the surgical tool. The slidable mass includes a proximal end, a substantially open distal end, and a side wall extending therebetween and defining an inner lumen. The side wall includes a longitudinally extending opening formed therein and in communication with the inner lumen. In use, the slidable mass is rotatably movable between a first orientation, in which the mass is slidably and operably mated to the surgical tool, and a second orientation in which the mass is removable from the surgical tool. When the mass is positioned in the first orientation, the mass can be slidably moved along a longitudinal axis of the surgical tool to apply a force to the tool.

In another embodiment, the handle portion of the surgical tool includes a proximal end, a distal end, and four sides extending therebetween. A first pair of opposed sides can have a first shape, and the other pair of opposed sides can have a second shape. The first shape of the first pair of opposed sides can be, for example, substantially flat, and the second shape of the other two opposed sides can be, for example, substantially rounded. The opening in the side wall of the mass can have a shape complementary to the first shape of the two opposed sides of the handle to allow the handle to be disposed around the mass. In a preferred embodiment, the two opposed, substantially flat sides have a first width, the other two opposed substantially rounded sides have a second width, and the width of the groove is greater than the first width, and less than the second width.

The groove or opening in the sidewall of the mass is useful in that it allows access to the hollow inner portion of the impacting device, enabling a surgical tool to be mated with the impacting device. A tool suitable for mating with the impacting device is one in which the handles of the tool will fit within the groove in a first orientation, but not in second orientation. Once the tool is mated with the impacting device, the tool is rotated 90° to a locked position to prevent removal of the tool through the groove. While in the locked position the impacting device is able to be manually reciprocated along the longitudinal axis of the tool.

The slidable mass is used to insert the tool (or an attached device) within an orthopedic structure, or remove the tool (or an attached device) from within an orthopedic structure by applying a force to the surgical tool. The distal end of the surgical tool may have formed thereon a bone preparation device (e.g., a rasp), a trial device, a connection element that allows the tool to attach to another device, or another surgically useful element. The preparation device and the trial device may be integral with the elongate member or they may be selectively attached to the elongate member through the connection element.

In another embodiment, the proximal end of the slidable mass can include an inner, substantially flattened proximal end wall, and an inner, substantially tapered distal end wall having a central opening extending therethrough. The slidable mass is effective to apply a proximally directed force to the inner, proximal end wall and a distally directed force to the inner, distal end wall. In a preferred embodiment, the slidable mass has a length greater than a length of the handle portion of the surgical tool. The mass is movable between a first proximal position, in which the open distal end of the mass abuts the distal end of the handle portion and the proximal end of the mass is positioned proximal to the proximal end of the handle portion, and a second position, in which the proximal end of the mass abuts the proximal end of the handle portion and the distal end of the mass is positioned distal to the distal end of the handle portion.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
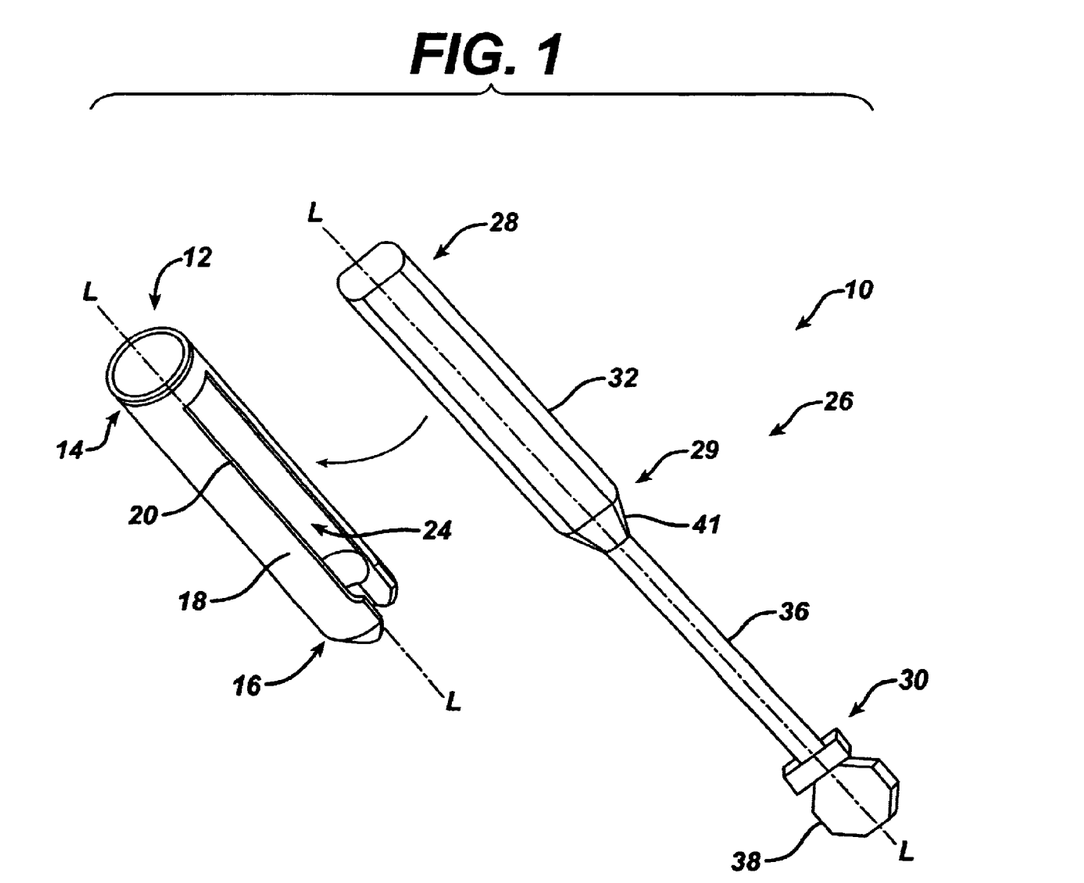
FIG. 1 is a perspective view of components the surgical system of the invention in an unmated condition.

The present invention pertains to a force applying surgical system that can be used to assist in the insertion or removal of a surgical tool (or a device attached thereto) from an orthopedic structure. This surgical system 10, as shown in FIG. 1, generally includes a medical impacting device 12, e.g., a slidable mass, that mates with a surgical tool 26 such that the impacting device 12 can be manually reciprocated along an axis L of the tool 26 to forcefully impact the impacting device 12 on a portion of the tool 26. The impacting device 12 can generate a distally directed force for inserting the tool 26 (and/or an attached device) into an orthopedic structure, or it can generate a proximally directed force to remove the tool 26 (and/or an attached device) from an orthopedic structure.

Figure 2:
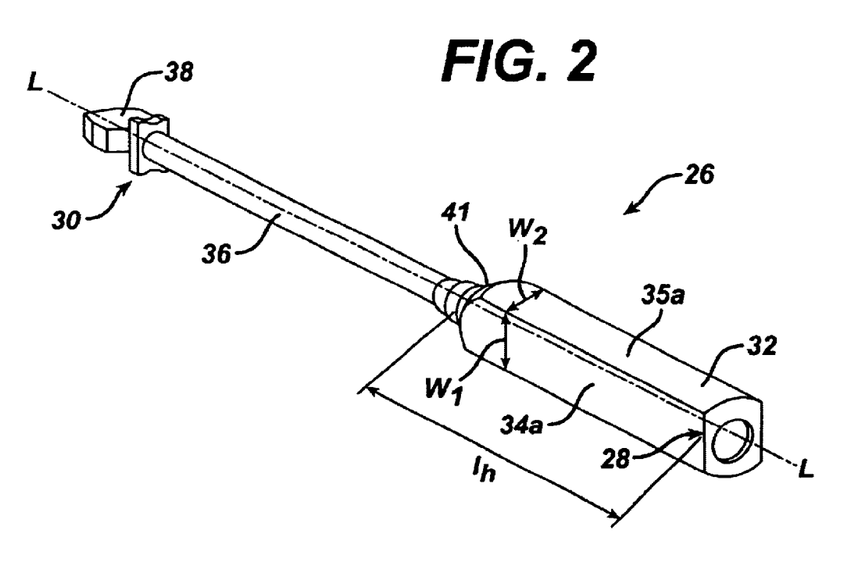
FIG. 2 is a perspective view of one embodiment of a surgical tool useful with the system of the present invention.

FIGS. 1 and 2 illustrate an exemplary surgical tool 26 that is useful with the surgical system 10. As shown, the surgical tool 26 is generally elongated and includes a proximal end 28 having a handle portion 32, and a distal end 30. An elongate member 36 extends from a distal end 29 of the handle portion 32, and terminates at distal end 30. The handle portion 32 of the tool 26 can have a variety of shapes and sizes, but it preferably has proximal and distal ends 28, 29, and four sides: a first pair of opposed sides 34a, 34b having a first shape, and the other two opposed sides having a second shape 35a, 35b. While the shape of each side 34a, 34b, 35a, 35b can vary, opposed sides 34a and 34b preferably have a substantially flat shape, and opposed sides 35a, 35b preferably have a substantially rounded shape. The proximal and distal ends 28, 29 of the handle portion can also vary in shape and size, but preferably the proximal end 28 of the handle portion 32 has a substantially flat shape, and the distal end 26 is tapered to form a shoulder 41. The tapered shoulder 41 allows for better visualization of the surgical field.

In an exemplary embodiment, the handle 32 has a length $l_h$ that is less than a length $l_m$ of impacting device 12 to enable reciprocating movement of the device 12 with respect to the handle 32. Preferably, the length differential should be such that it allows for about 5 mm to 150 mm of travel of the device 12. The width of the handle portion 32 can also vary, but preferably the handle 32 includes first and second widths $w_1$, $w_2$, as shown in FIG. 2. The first width $w_1$ extends between the opposed, rounded sides 35a, 35b, and the second width $w_2$ extends between the opposed, flat sides 34a, 34b. The second width should be less than the first width $w_1$ to allow the handle portion 32 to mate with the impacting device 12 in only one of two orientations, as will be discussed in more detail below. In an exemplary embodiment, the first width $w_1$ is in the range of about 2.5 mm to 40 mm, and the second width $w_2$ is in the range of about 5 mm to 60 mm.

The elongate member 36, which extends from the distal end 29 of the handle portion 32, can include an instrument 38 that is formed integrally with or removably attachable to the distal end 30 of the tool 26. Although the instrument 38 is illustrated to be a rasp-type device, other devices may be present on the tool as well. For example, instrument 38 may be a trial device, such as a spinal implant trial, used to assess the fit of an implant of a given size and/or type. The tool 26 can optionally include a connection element, or attachment mechanism, formed on the distal end 30 that enables the tool to be selectively connected to another element such as a bone affecting element (e.g., a rasp device), a trial device, a prosthesis, a prosthesis component, or another surgical tool.

One of ordinary skill in the art will appreciate that a variety of surgical tools may be used with the present invention, and surgical tool 26 is only one example of a suitable tool. Virtually the only requirement of a suitable tool is that it have a structure, such as a handle, that is able to be mated with the hollow inner portion 24 of the impacting device 12. Accordingly, such a structure (e.g., a handle) should have dimensions to allow the tool to be insertable and removable from the impacting device 12 in a first orientation, and mated to the impacting device 12 in a second orientation. In the second orientation, the tool 26 is locked within the impacting device 12, such that it cannot be removed through groove 20. While locked in the second orientation, the impacting device 12 is still able to be manually reciprocated along the longitudinal axis L of the tool 26.

Figure 3:
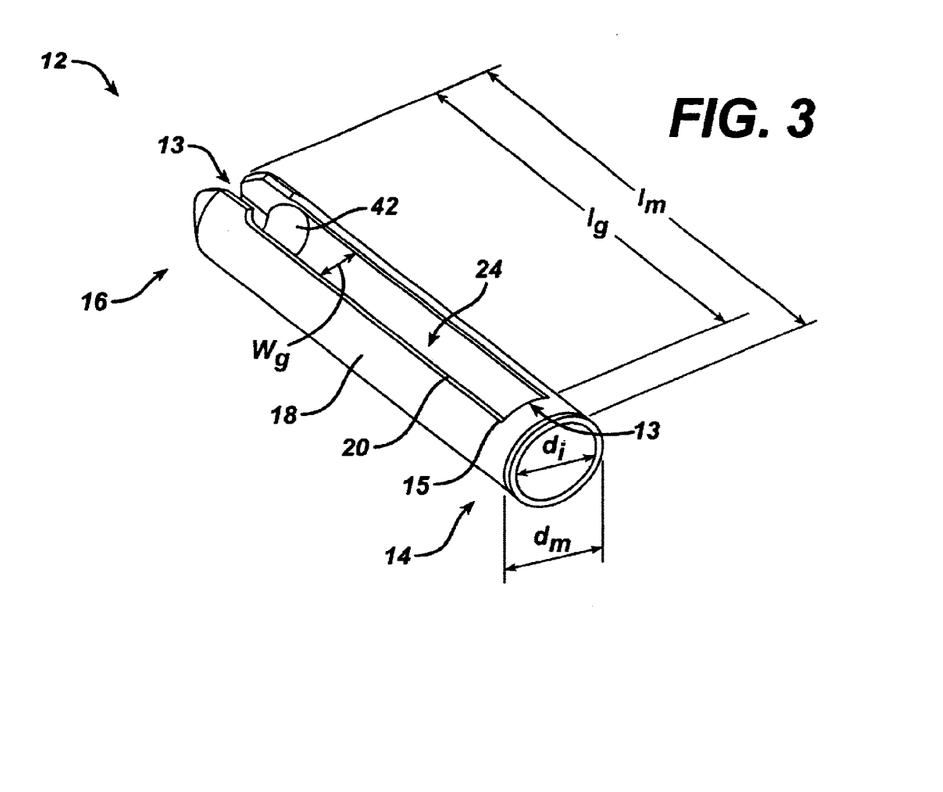
FIG. 3 is a perspective view of an embodiment the medical impacting tool of the present invention.

The handle portion 32 of the surgical tool 26 is adapted to mate with the medical impacting device 12, which is shown in more detail in FIG. 3. The impacting device 12 generally includes a proximal end 14 that is preferably substantially closed, a distal end 16 that is at least partially open, and a side wall 18 defining an inner lumen 24 that extends between the proximal and distal ends 14, 16.

Figure 4:
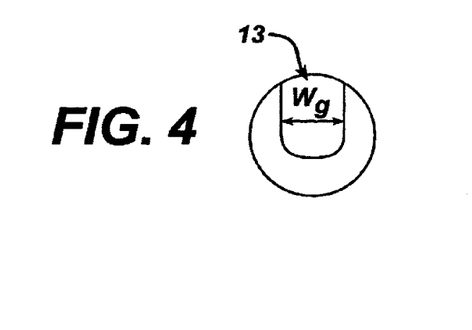
FIG. 4 is an end view of a distal end of the impacting device shown in FIG. 3.

The shape and size of the impacting device 12 can vary, but the device 12 preferably has a generally elongate cylindrical shape. The proximal and distal ends 14, 16 of the impacting device 12 are preferably adapted to conform to the shape of the proximal and distal ends 28, 26 of the handle 32. In one embodiment, the proximal end 16 of the impacting device 12 is substantially flat to receive the flat proximal end 28 of the handle portion 32 of tool 26, and the distal end 14 of the mass 12 is tapered to seat the shoulder 41 of the handle portion 32 of the tool 26. In an exemplary embodiment, the distal end 14 of the mass 12 and the distal end 26 of the handle 32 are tapered at an angle in the range of about 20° to 40°, and most preferably at about 30°. The distal end 26 can include an orifice 13 which is adapted to slidably receive the elongate extension 36 of the surgical tool 26. The orifice 13, shown in FIG. 4, can vary in shape and size, but it preferably has a width $w_o$ in the range of about 20 mm to 60 mm.

The side wall 18 of the impacting device 12 includes a groove 20, or opening, formed therein that extends parallel to the longitudinal axis L of the device 12. The groove 20 preferably has a length $l_g$ that causes it to occupy a majority of the length $l_m$ of the impacting device 12. More preferably, the groove 20 extends from the proximal end 14 at a point 15 distally adjacent to the proximal end 14, through the opening at the distal end 16. The opening created by the groove 20 communicates with the inner lumen 24 of the impacting device 12, and is adapted to receive the surgical tool 26.

The groove 20 can vary in shape and size, but it should be adapted to receive the surgical tool 26 when the impacting device 12 is positioned in a first orientation, and to be locked and slidably mated to the surgical tool 26 when the impacting device 12 positioned in a second orientation. Preferably, the width $w_g$ of the groove 20 is greater than the width $w_2$ between the flat sides 34a, 34b of the handle portion 32 of the surgical tool 26 such that the handle portion 32 of the tool 26 can be inserted with the flat sides 34a, 34b positioned adjacent the groove 20. Conversely, the width $w_g$ of the groove 20 is preferably smaller than the width $w_1$ between the rounded sides 35a, 35b of the handle portion 32 such that the handle portion 32 of the surgical tool 26 is retained, e.g., locked, within the inner lumen 24 of the impacting device 12. The tool 26, when in the locked position, is slidably movable along the longitudinal axis L of the tool 26.

In an exemplary embodiment, the width $w_g$ of the groove is in the range of about 8 mm to 30 mm. The length $l_g$ of the groove can also vary, but the length $l_g$ should be greater than the length $l_h$ of the handle portion 32 of the tool 26, and less than the length $l_m$ of the impacting device 12. Preferably, the length $l_g$ of the groove 20 is in the range of about 80 mm to 350 mm, and the length $l_m$ of the impacting device 12 is in the range of about 85 mm to about 380 mm.

Figure 5:
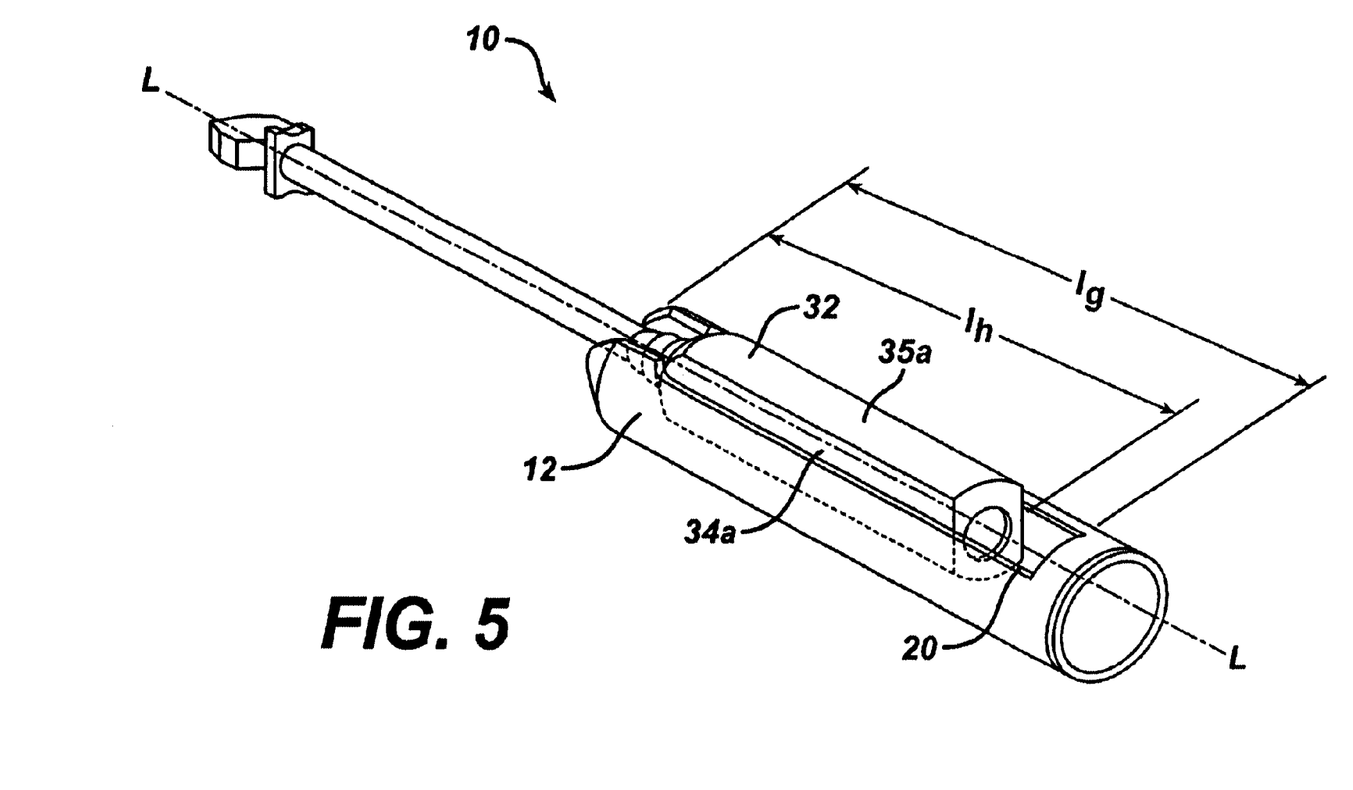
FIG. 5 a perspective view of the system of FIG. 1 in which a surgical tool is partially inserted into the medical impacting device.
Figure 6A:
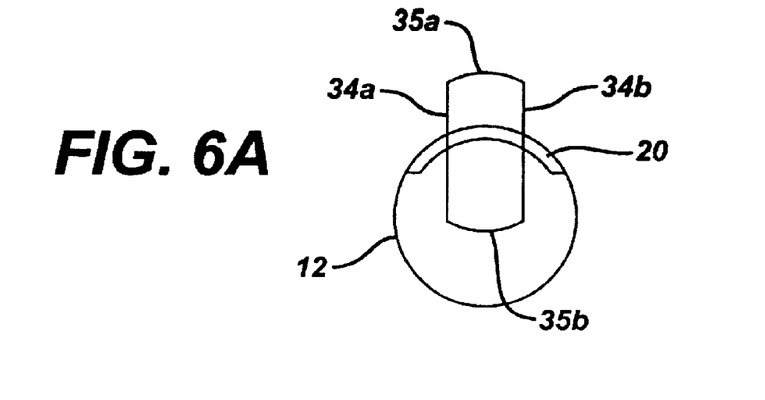
FIG. 6A a proximal end view of the system of FIG. 1 in which a surgical tool is partially inserted into the medical impacting device.
Figure 6B:
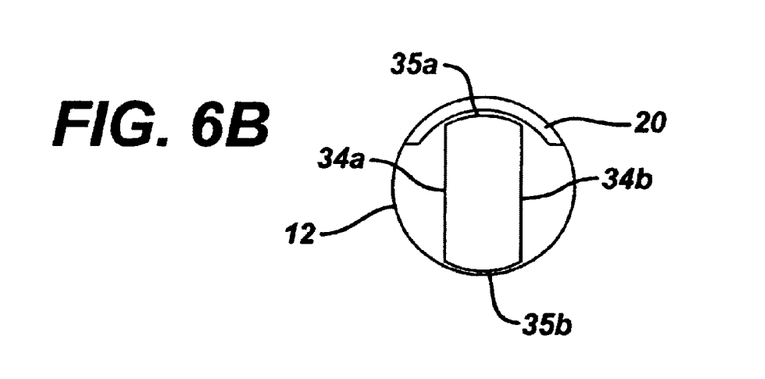
FIG. 6B a proximal end view of the system of FIG. 1 in which a surgical tool is fully inserted into the medical impacting device in an unlocked condition.

FIGS. 5 and 6A depict the initial engagement of the surgical tool 26 with the medical impacting device 12. The handle 32 of the tool 26 is oriented in a first, insertion position to allow it to fit through the groove 20 of the impacting device. In the insertion position, the substantially flat surfaces 34a, 34b of the handle 32 are aligned to be adjacent to the edges of the side wall 18 that define groove 20. As shown in FIG. 6B, continued insertion of the tool 26 within the impacting device 12 results in the handle 32 being fully seated within the inner hollow portion 24 of device 12 in an unlocked position. In the unlocked position, the handle 32 is oriented so that it can be lifted through the groove 20 to be removed from the impacting device 12. As so positioned, the entire handle 32 is disposed within device 12 and, depending on the location of the device 12, a portion of the elongate member 36 resides within a portion of the groove 20 as well. Regardless of the position of device 12, a portion of elongate member 36 emerges from the distal opening of the device 12.

Figure 6C:
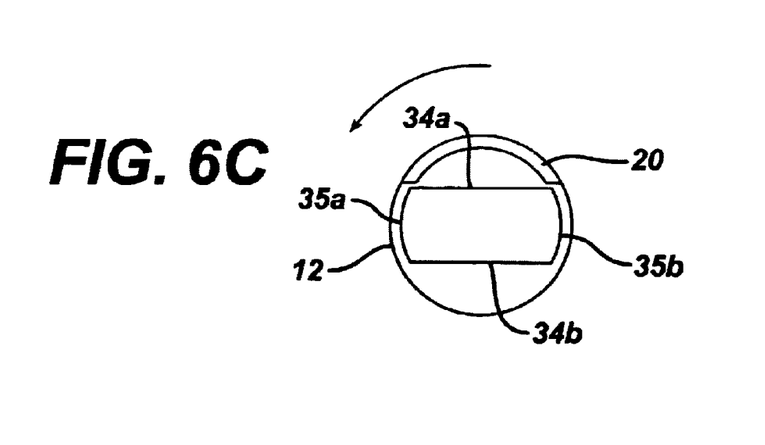
FIG. 6C is a proximal end view of the system of FIG. 1 in which the surgical tool is fully inserted and locked within the medical impacting device.

Once the handle 32 has been completely inserted within the impacting device 12, as shown in FIG. 6B, the tool 26 can be locked within the device 12 by rotating the handle 32 approximately 90° such that one of the flat surfaces 34a, 34b is aligned with and visible through the opening formed by the groove 20 in the side wall 18 of the impacting device 12. FIG. 6C illustrates the handle portion 32 of the tool 26 in the locked position, in which the handle 32 of tool 26 is oriented so that the wider dimension of the handle is not able to fit through groove 20 to separate the tool 26 and the impacting device 12.

The locking of the tool 26 within the medical impacting device 12 does not prevent reciprocating movement of the device 12 relative to the tool 26 along the longitudinal axis L of tool 26. As FIG. 5 depicts, the length $l_h$ of the handle 32 is less than the length $l_g$ of the groove 20, enabling the device 12 to be selectively reciprocated along the longitudinal axis L of the tool 40.

In use, the impacting device 12 is effective to insert or remove tool 26 (or an attached device) from an orthopedic structure by forcefully moving the impacting device 12 along the tool 26 in the either a proximal or distal direction. When moved in the proximal direction, the distal portion 16 of the of the device 12 impacts on a distal portion 29 of the handle 32. In one embodiment, as shown in FIGS. 1 and 5, the distal portion 16 of the handle 32 has a shoulder 41 which is impacted by the tapered distal end 16 surrounding the orifice 13 of the impacting device 12 when the device 12 is moved in the proximal direction. Conversely, to insert tool 26 (or an attached device) within an orthopedic structure, the impacting device 12 is forcefully moved along the tool 26 in the distal direction so that an inner end wall (not shown) at the proximal end 14 of the device 12 impacts on the proximal end wall 28 of handle 32. One of ordinary skill in the art will appreciate that one or more impacts may be necessary, depending on the mass of the impacting device 12, for a removal or insertion procedure. While the mass of the impacting device 12 can vary, the mass is preferably in the range of about 225 g to 1375 g.

The components of the surgical system 10 can be formed from a variety of materials. The material should have sufficient strength so as to withstand applied pressures to insert or remove a surgical instrument. Suitable materials include biocompatible materials such as stainless steel. Exemplary materials include a variety of medically acceptable metals, metal alloys, ceramics, and plastics. The components of the surgical system 10 can be comprised of a heterogeneous mixture of biocompatible materials. The inner surface of the inner lumen 24 of the device 12 can be made from the same material that forms device 12, or alternatively it can be coated or covered with a biocompatible material, such as a polymer, ceramic or a metal.

One of ordinary skill in the art will further appreciate further features and advantages of the invention based on the embodiments described above. All references referred to herein are expressly incorporated by reference in their entirety.

What is claimed is:

1. A surgical system, comprising:
   an elongate surgical tool having a proximal handle portion having a proximal end, a distal end, and two opposed, substantially flat sides extending therebetween, and a distal portion extending from the proximal handle portion; and
   a substantially cylindrical, hollow slidable mass removably and replaceably disposed around the handle portion of the elongate surgical tool and rotatably movable between a first orientation and a second orientation, the slidable mass having a proximal end, a substantially open distal end, and a side wall extending therebetween and defining an inner lumen, the side wall having a longitudinally extending opening formed therein and in communication with the inner lumen;
   wherein the slidable mass is slidably operable and mated to the surgical tool when the mass is positioned in the first orientation, and removable from the surgical tool when the mass is positioned in the second orientation.

2. The surgical system of claim 1, wherein the slidable mass is slidably movable along a longitudinal axis of the surgical tool when positioned in the first orientation.

3. The surgical system of claim 2, wherein the opening in the side wall of the slidable mass is sized to receive the handle portion of the elongate surgical tool when the mass is positioned in the second orientation.

4. The surgical system of claim 3, wherein the opening in the side wall defines opposed edges, and wherein the slidable mass is positioned in the second orientation when the opposed edges of the side wall are positioned adjacent the two opposed, substantially flat sides of the handle portion of the elongate surgical tool.

5. The surgical system of claim 1, wherein the open distal end of the slidable mass is adapted to slidably seat the distal portion of the surgical tool.

6. The surgical system of claim 1, wherein the proximal end of the slidable mass includes an inner, substantially flattened proximal end wall, and an inner, substantially tapered distal end wall having a central opening extending therethrough, the slidable mass being effective to apply a proximally directed force to the inner, substantially flattened proximal end wall of the surgical tool and a distally directed force to the inner, substantially tapered distal end wall of the surgical tool.

7. The surgical system of claim 1, wherein the slidable mass has a length greater than a length of the handle portion of the surgical tool.

8. The surgical system of claim 1, wherein the slidable mass is movable between a first, proximal position in which the open distal end of the mass abuts the distal end of the handle portion of the surgical tool and the proximal end of the mass is positioned proximal to the proximal end of the handle portion of the surgical tool, and a second position in which the proximal end of the mass abuts the proximal end of the handle portion of the surgical tool and the distal end of the mass is positioned distal to the distal end of the handle portion of the surgical tool.

9. The surgical system of claim 1, wherein the handle portion of the elongate surgical tool includes four sides, wherein a first pair of opposed sides have a substantially flat shape and define a first width, and a second pair of opposed sides define a second width, and wherein the opening in the side wall of the slidable mass defines a third width, the third width being greater than the first width and less than the second width.

10. The surgical system of claim 1, wherein the distal portion of the surgical tool includes a distal end having an attachment mechanism disposed thereon and selectively connectable to an element selected from the group consisting of a prosthesis, a prosthesis component, and a medical instrument.

11. A surgical system, comprising:
   an elongate surgical tool having a proximal handle portion with four sides, two opposed sides having a first shape, and the other two opposed sides having a second shape, and an elongate member extending distally from the handle portion and terminating at a distal end; and
   a slidable mass removably and replaceably engageable with the surgical tool to enable the slidable mass to be selectively reciprocated along a longitudinal axis of the surgical tool, the slidable mass having
   a substantially closed proximal end, a substantially open distal end, and a side wall defining a hollow inner portion within which a portion of the surgical tool is able to seat, and
   a longitudinally extending groove formed in at least a portion of the side wall, the groove extending distally from a point adjacent the proximal end of the device and forming an opening in the side wall that communicates with the hollow inner portion of the slidable mass.

12. The surgical system of claim 11, wherein the slidable mass is slidably and operably mated to the handle portion of the surgical tool when the mass is positioned in a first orientation, and the slidable mass is removable from handle portion of the surgical tool when the mass is positioned in a second orientation.

13. The surgical system of claim 12, wherein the opening in the side wall of the slidable mass defines a shape complementary to the first shape of two opposed sides of the handle.

14. The surgical system of claim 13, wherein the slidable mass is movable along a longitudinal axis of the surgical tool when the mass is positioned in the first orientation.

15. The surgical system of claim 11, wherein the substantially open distal end of the mass is adapted to slidably seat the elongate member extending distally from the handle portion.

16. The surgical system of claim 11, wherein the handle portion of the surgical tool includes two opposed, substantially flat sides having a first width, and two opposed substantially rounded sides having a second width, and the groove in the slidable mass defines a width greater than the first width and less than the second width.

17. The surgical system of claim 11, wherein the distal end of the elongate member is adapted to selectively mate to an element selected from the group consisting of a prosthesis, a prosthesis component, and a medical instrument.

18. The surgical system of claim 11, wherein the slidable mass is effective to selectively apply a proximally directed force and a distally directed force to the surgical tool.

19. A medical impacting device, comprising:
   an elongate, substantially cylindrical object having a side wall defining a hollow inner portion, a longitudinal axis, a substantially closed proximal end, and an open distal end; and
   a longitudinally extending groove formed in at least a portion of the side wall and in communication with the hollow inner portion of the cylindrical object, the groove extending from the open distal end to a point adjacent the proximal end of the cylindrical object;

wherein the groove and the hollow inner portion of the object have geometries and dimensions suitable to facilitate selective, sliding engagement with a portion of a surgical tool in a manner that enables the impacting device to be reciprocated along the longitudinal axis thereof to apply a force to a portion of the surgical tool.

* * * * *